Aug. 13, 1935. J. H. NICOLAS Plant Pat. 132
ROSE
Filed March 13, 1935
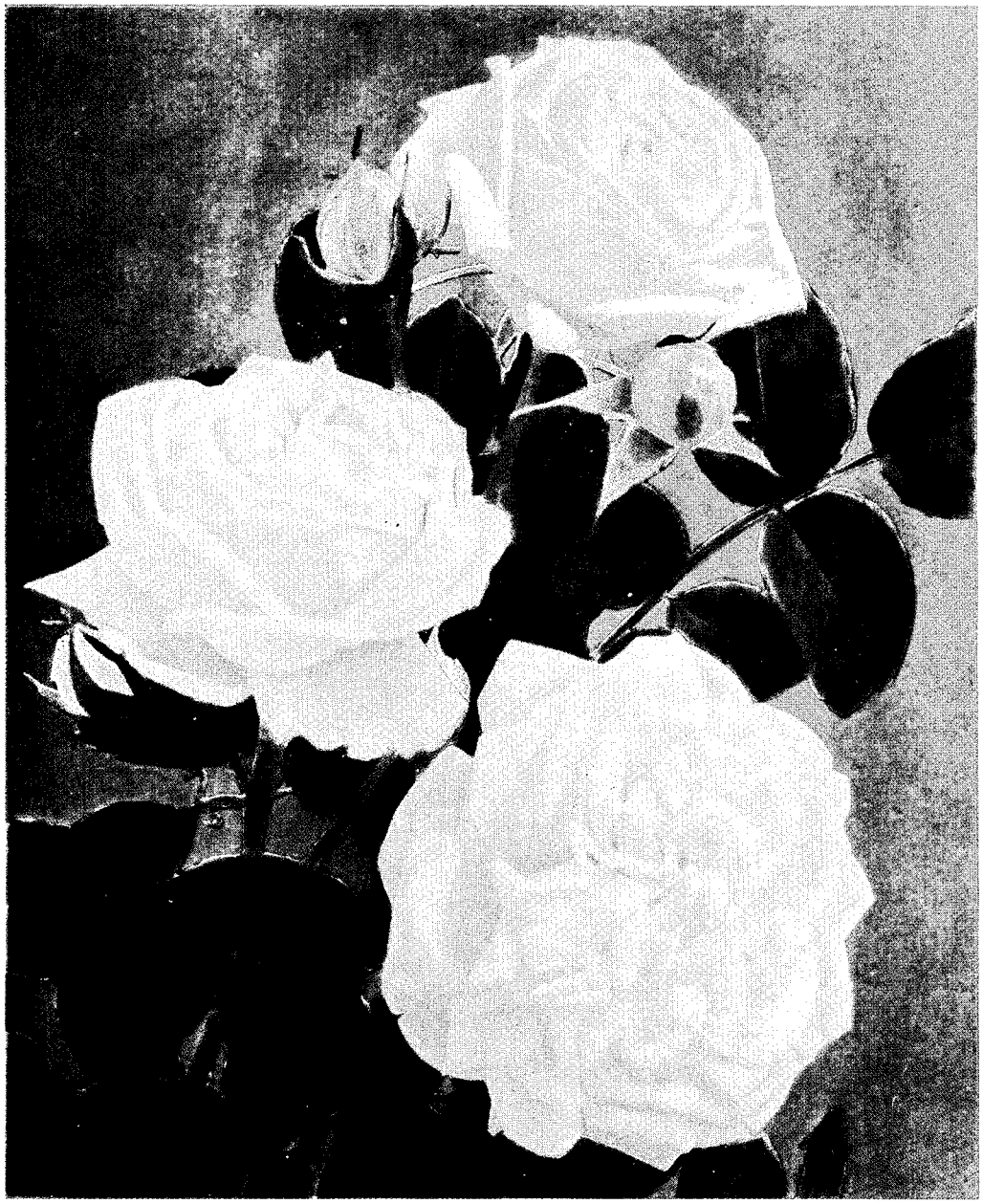
Inventor
Jean H. Nicolas
By Robert Robb
Attorney Patented Aug. 13, 1935

Plant Pat. 132

UNITED STATES PATENT OFFICE

132

ROSE

Jean H. Nicolas, Newark, N. Y., assignor to Jackson & Perkins Company, Newark, N. Y.

Application March 13, 1935, Serial No. 10,946

1 Claim. (Cl. 47—61)

The present new and distinct variety of rose plant is the result of a definite effort to produce a white rose, everblooming, perfumed, easy to grow and hardy almost anywhere in the United States.

The perfection of such a plant was a development problem of considerable magnitude, but the present invention has been developed as the answer to all the requirements, by virtue of the interbreeding of known varieties having the desired characteristics, giving rise to a highly complex hybrid of very diverse usage.

In this respect, it is notable that the new variety possesses distinction because it may be used as a large shrub, a hedge, or a pillar, but because of the fact that it stands close pruning, it can also be used as Hybrid Tea bedding variety.

A further claim of novelty resides in its great hardiness which was derived from the crossing of two of the hardiest species known, the R. Nutkana from Alaska and the R. Rugosa from Siberia. More specifically its pedigree may be stated as follows: R. Nutkana x Paul Neyron (known in commerce as "Schoener's Nutkana") and R. Rugosa Alba x Clotilde Soupert (known in commerce as "New Century").

From this ancestry it has acquired the hardiness and vegetation of the species (having by way of test withstood 28° below zero F., without appreciable injury), the well-known fullness of the Paul Neyron variety, the color, form and continuity of bloom of the Clotilde Soupert, and the strong, composite perfume of Centifolia (Paul Neyron) and the wild rose. It may also be considered as a new everblooming type of Hybrid Perpetual.

With reference to its habits of growth, it may be noted that the plant can be left to grow into a large shrub, with canes rising to ten feet in height which can be used as a pillar. It also makes a splendid hedge material and because it will stand close pruning as a vigorous Tea, as before premised, it can thus be used for bedding or mass planting.

Its important novel and distinctive characteristics, including (1) it diversity of usage and (2) its greater resistance to cold than any other everblooming shrub or bush rose, have been by asexual reproduction proved to be permanent or fixed.

The following is a detail description of this variety:

Parentage:

Seedling.

*Seed parent.*—Schoener's Nutkana (R. Nutkana x Paul Neyron).

*Pollen parent.*—New Century (Rugosa Alba x Clotilde Soupert).

Classification:

*Botanic.*—Nutkana-Rugosa Hybrid.

*Commercial.*—Hybrid Perpetual or Tea.

*Flower*

Blooming habit:

Continuous.

Bud:

*Size.*—Medium.

*Form.*—Globular. Unaffected by wet or hot weather.

*Color.*—When sepals first divide rosy carmine; when petals begin to unfurl blush white. When petals half blown blush inside of petals and reverse of petals white. (Gravereaux color system.)

*Sepals.*—Branched slightly; stand up.

*Calyx.*—Pear shaped. Size large. Aspect glandular. Odor when rubbed none.

*Peduncle.*—Medium length. Aspect rough. Color light green. Strength bending.

*Opening.*—Opens well. May ball in very wet weather.

Bloom:

*Size.*—Medium; average size when fully expanded 3 to 3½ inches.

*Borne.*—Singly or several together.

*Stems.*—Long; normal strength.

*Form.*—When first open globular.

*Permanence.*—Retains its form to the end.

*Petalage.*—Very double (many petals and stamens hidden). Number of petals under normal conditions 100.

*Color.*—Center of flower light blush. Outer petals white. Base of petals (aiglet) greenish. Inside of petals white. Reverse of petals white.

*Discoloration.*—General tonality at end of first day light blush. Second day paler to almost white. Third day pure white.

Petals:

*Texture.*—Soft; unaffected by hot weather; may ball in wet weather.

*Appearance.*—Inside satiny; outside satiny.

*Form.*—Round; slightly scalloped.

*Arrangement.*—Imbricated; quartered sometimes. Petaloids in center; many and small.

*Persistence.*—Hang on and dry.

*Fragrance.*—Strong, "Old Rose Perfume" (Centifolia) combined with wild rose.

*Lasting quality.*—On the plant and as a cut flower very long.

Genital organs:

*Stamens, anthers.*—Small, few. Color—white. Arrangement—mixed with petaloids.

*Stamens, filaments (threads).*—Medium length. Color—white.

*Pollen.*—White.

*Styles.*—Bunched, loosely separated, uneven length.

*Stigmas.*—White color.

*Ovaries.*—Some protruding from calyx.

Fruit:

Variety is seldom fertile with its own pollen, but fruits with strange pollen.

*Form.*—Round headed.

*Aspect.*—Rough.

*Color at maturity.*—Orange.

*Sepals.*—Caducous (soon falling).

*Plant*

Form:

Bush, shrub or pillar.

Growth:

Very vigorous, upright, branching.

Foliage:

Generally five leaflets, often seven.

*Size.*—Medium.

*Quantity.*—Normal.

*Color.*—New foliage—upper side normal green; under side lighter green, rough. Old foliage—upper side dark green; under side lighter green.

*Shape.*—Oval pointed.

*Texture.*—Upper side leathery; under side rough; ribs prominent.

*Edge.*—Serrated (saw toothed).

*Serration.*—Single, small.

*Leaf stem.*—Reddish color; under side rough.

*Stipules.*—Medium length; bearded.

*Disease resistance.*—Resistant.

Wood:

*New wood.*—Color light green; bark rough.

*Old wood.*—Color green, brown; bark rough.

Thorns: (Divided into thorns, prickles and short needles).

*Thorns.*—Quantity—on main stalks from base many; on laterals from stalks ordinary. Form—narrow base; medium length; straight. Color when young—red. Position—Irregular.

*Prickles.*—Quantity—on main stocks many; on laterals few. Color—brown.

*Short needles.*—Quantity—on main stalks none. On laterals none.

I claim:

A new and distinct variety of rose plant, characterized by its habits of growth which permit of diversity of usage as a pillar, everblooming Hybrid Perpetual shrub or bedding plant, and its greater resistance to cold than any other everblooming shrub or bush rose, combined with the color and strong fragrance of its blooms, as herein shown and described.

JEAN H. NICOLAS.